(12) United States Patent
Stone et al.

(10) Patent No.: US 11,236,298 B2
(45) Date of Patent: Feb. 1, 2022

(54) SYSTEM FOR USE IN BIOPROCESSING

(71) Applicant: TTP Plc, Royston (GB)

(72) Inventors: Edwin Stone, Royston (GB); Peter Crossley, Royston (GB)

(73) Assignee: TTP Plc, Royston (GB)

( * ) Notice: Subject to any disclaimer, the term of this patent is extended or adjusted under 35 U.S.C. 154(b) by 414 days.

(21) Appl. No.: 16/302,304

(22) PCT Filed: May 24, 2017

(86) PCT No.: PCT/GB2017/051459
§ 371 (c)(1),
(2) Date: Nov. 16, 2018

(87) PCT Pub. No.: WO2017/203249
PCT Pub. Date: Nov. 30, 2017

(65) Prior Publication Data
US 2019/0292507 A1    Sep. 26, 2019

(30) Foreign Application Priority Data

May 24, 2016    (GB) .................................... 1609084

(51) Int. Cl.
*C12M 1/00*    (2006.01)
*C12M 1/26*    (2006.01)
*C12M 1/34*    (2006.01)

(52) U.S. Cl.
CPC ............ *C12M 23/28* (2013.01); *C12M 23/26* (2013.01); *C12M 23/34* (2013.01); *C12M 29/18* (2013.01); *C12M 33/00* (2013.01); *C12M 41/36* (2013.01)

(58) Field of Classification Search
None
See application file for complete search history.

(56) References Cited

U.S. PATENT DOCUMENTS

| 2,913,862 | A |   | 11/1959 | Sabee |
| 5,027,577 | A |   | 7/1991  | Creswick |
| 2003/0230521 | A1 | * | 12/2003 | Schick ................... B01D 61/20 210/110 |
| 2010/0296968 | A1 |   | 11/2010 | Cady |
| 2012/0009588 | A1 |   | 1/2012  | Rajagopal et al. |

(Continued)

FOREIGN PATENT DOCUMENTS

| DE | 197 10 241 | A1 | 11/1997 |
| DE | 19710241   | A1 | 11/1997 |

(Continued)

OTHER PUBLICATIONS

Notification of Transmittal of the International Search Report and the Written Opinion of the International Searching Authority, or the Declaration dated Aug. 25, 2017, in International Application No. PCT/GB2017/051459; Filed: May 24, 2017; Applicant: THE TECHNOLOGY PARTNERSHIP PLC.

(Continued)

*Primary Examiner* — Holly Kipouros
(74) *Attorney, Agent, or Firm* — Erise IP, P.A.

(57) ABSTRACT

A consumable container for filling with a fluid in a bioprocessing process. The container comprises one or more sealable, removable portions, such that one or more samples of the fluid may be taken by sealing and removing one or more of said portions.

26 Claims, 7 Drawing Sheets

(56) References Cited

U.S. PATENT DOCUMENTS

| | | | |
|---|---|---|---|
| 2012/0184033 A1* | 7/2012 | Crimmins | A61M 1/0272 435/374 |
| 2013/0203106 A1* | 8/2013 | Shvets | C12M 23/08 435/32 |
| 2014/0076454 A1* | 3/2014 | Kjar | A61M 39/223 141/1 |
| 2016/0122798 A1 | 5/2016 | Zhang et al. | |
| 2016/0123848 A1 | 5/2016 | Griffin et al. | |
| 2017/0362556 A1* | 12/2017 | Ali | C12M 37/00 |

FOREIGN PATENT DOCUMENTS

| | | |
|---|---|---|
| EP | 1 548 420 A2 | 6/2005 |
| EP | 1548420 A2 | 6/2005 |
| EP | 2 248 723 A1 | 11/2010 |
| EP | 2248723 A1 | 11/2010 |
| JP | 2006 089136 A | 4/2006 |
| JP | 2006089136 A | 4/2006 |
| WO | 2012092394 A1 | 7/2012 |
| WO | 2014/012584 A1 | 1/2014 |

OTHER PUBLICATIONS

European Patent Application No. 21173713.5 European Search Report dated Sep. 6, 2021.
Database WPI, Week 200628, Thomson Scientific, London, GB, AN 2006-267932 XP002773037, & JP2006089136 A, Abstract, Sanko Kikai Co. Ltd., Apr. 6, 2006.

* cited by examiner

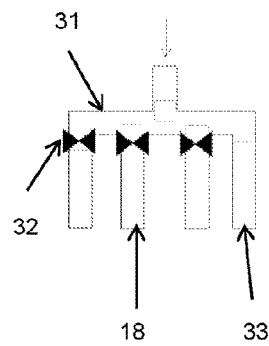 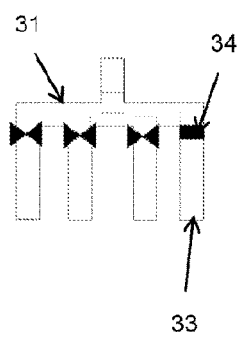 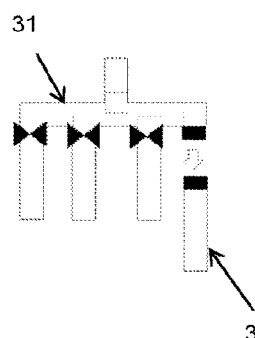 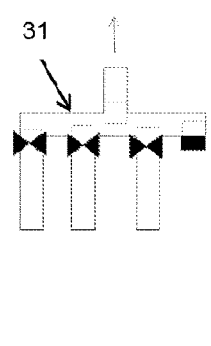
Figure 4a　　　Figure 4b　　　Figure 4c　　　Figure 4d
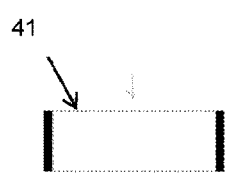 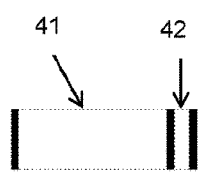 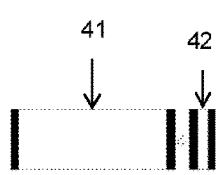 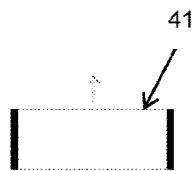
Figure 5a　　　Figure 5b　　　Figure 5c　　　Figure 5d

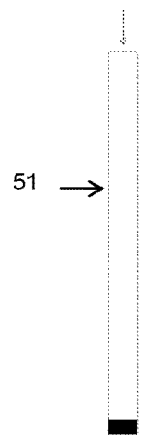 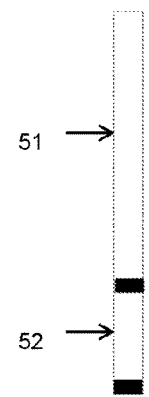  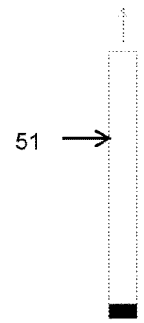
Figure 6a  Figure 6b  Figure 6c  Figure 6d
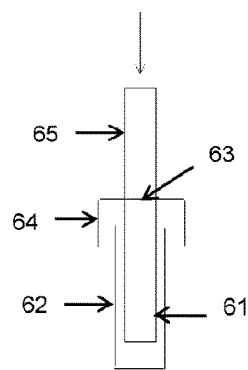 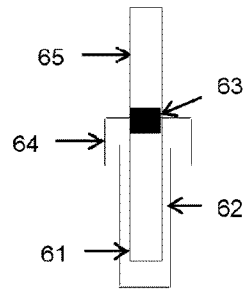 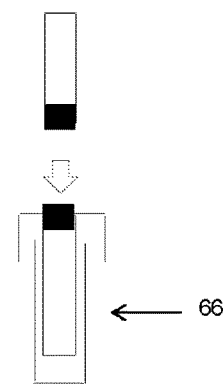 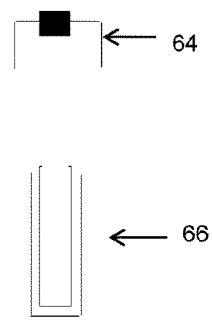
Figure 7a  Figure 7b  Figure 7c  Figure 7d

SYSTEM FOR USE IN BIOPROCESSING

RELATED APPLICATIONS

The present application is a national stage application under 35 U.S.C. § 371 of International Application No. PCT/GB2017/051459, filed 24 May 2017, which claims priority to Great Britain Patent Application No. 1609084.7, filed 24 May 2016. The above referenced applications are hereby incorporated by reference into the present application in their entirety.

FIELD

The present invention relates to a system for use in bioprocessing.

BACKGROUND

In bioprocessing it is often necessary to remove a sample from a larger volume of a product, such as for analysis of the sample for the purpose of quality assurance. Because of the nature of such bioprocessing, several design constraints are imposed on systems for removing such samples. For example, the removal of samples must be carefully controlled to avoid modifying or damaging the samples, and the samples must be of a minimum possible volume to avoid wasting potentially expensive product. Furthermore, such systems should be structured so that the process is aseptic, to avoid contamination of the product or samples. Many areas of biological research, for example autologous cell therapies, can also require that samples be taken at specific times, and that any samples be traceable. Variation in timing compared to the expected timing will lead to uncertainty over the validity of the result. For example, in a cell expansion process, taking a sample late could lead an incorrect assessment of the rate of expansion. A failure to ensure traceability could lead to analysing an incorrect sample. In the worst case this could lead to an unsafe product being declared safe. It is also desirable that such a system be low cost. Developing such systems therefore presents many challenges, and currently, therefore, sampling is often done manually.

One example of a manual process of removing a sample from a larger volume of a product relates to the removal of a sample from a WAVE Bioreactor, as produced by GE Healthcare Life Sciences. In such bioreactors a product is held within a disposable bag and rocked to provide mixing and gas transfer. When a sample is taken the movement of the product must be stopped and the user must prepare a sample port, for example by wiping with alcohol. The user must then connect a syringe to the sample port and tip the product bag so that the sample may be aspirated into the syringe. The movement of the product may only be restarted after the syringe has been removed. Finally, the sample must be transferred from the syringe into a format suitable for processing in an analysis system, for example a vial.

Such a manual process has numerous drawbacks, however. The first of these is that, in order for a sample to be taken, the product movement must be stopped, and this interruption will be for a variable period of time, potentially leading to product variability. There are also issues with the sampling method itself not being completely closed or completely controlled. As mentioned above, it is important to ensure that the sample and product are not contaminated and that they are not damaged. However, the interface between the syringe and the product is not completely sealed, leading to potential contamination, and the aspiration is not completely controlled, potentially leading to damage of the product and sample. There is also the issue that the sample volume may be larger than necessary. Additionally, the timing of the sampling is dependent on the user as the process is highly user intensive.

The present invention aims to solve this and other issues by providing a means of taking samples of a product which is easily automated and which is resistant to damage or contamination of the product and sample and allows for reliable traceability.

A further problem is that once the sample is taken it needs to be analysed. Common analyses can include cell viability and cell counting through first staining the cells and then imaging using an appropriate system. Other analytical approaches will look at cell phenotype using a fluorescent label and a flow cytometer. Further they can include molecular analysis, studying a cell's DNA with PCR, or alternatively a biomarker such as protein expression by the cells by using an immuno-assay. Other assays can look for contamination such as bacterial, fungal, or viral.

Typically a sample is taken from a bioreactor, transported to an area appropriate for sample preparation and then moved on for subsequent analysis. When working with biological samples, this will typically require biological containment to both protect the operator and to ensure the sample is not contaminated. There is variability and cost associated with both the sample transport and the analysis of the sample due to the operator involvement. The need for containment also presents a significant cost burden.

SUMMARY OF INVENTION

According to a first aspect of the invention, a consumable container is provided, said consumable container for filing with a fluid in a bioprocessing process and comprising one or more sealable, removable portions, such that one or more samples of the fluid may be taken by sealing and removing one or more of said portions.

In contrast to the manual process of taking samples of a product, the present invention ensures that, if attached to a rocking bioprocessor, the movement of said product need not be stopped to allow aspiration of a syringe, thereby preventing product variability. The sampling is also completely aseptic and controlled, preventing both contamination and product damage, and further ensuring that no more product is taken than is necessary.

The consumable container is also suitable for easy automation of the sampling process. The manual process described above is difficult to automate and is therefore highly user intensive. By allowing for automation of the sampling, the user may focus on other tasks, and the sample may be taken at any time.

An aspect of the present invention aims to solve some of the problems associated with the prior art by directly coupling the analytical process to the sampling process. The analytical process is often automated to avoid operator variation and cost. The process is inherently "closed" to avoid contamination and safety risks.

A further benefit is that whereas previously the sample would have to be transferred from the syringe into a format suitable for processing in an analysis system (for example a vial), or for easy transfer in a lab transport system (for example a pneumatic tube system), the present invention ensures that the sample may be taken in a format already suitable for analysis. This helps to prevent contamination of the sample.

Different methods may be employed to seal the one or more sealable, removable portions. The one or more sealable, removable portions may be sealed by application of heat to an area between the removable portion and the remainder of the consumable container, or in another embodiment the one or more sealable, removable portions may be separated from the remainder of the consumable container by respective physical, aseptic connectors, said connectors allowing sealing and removal of respective associated portions. If the portions are to be sealed by application of heat, the consumable container will preferably comprise a heat sealable material.

The one or more removable portions may be connected to a common transverse part in parallel or they may be connected in series. Samples may also be taken by removing portions of the bulk consumable container.

The consumable container of the present invention will preferably comprise a biocompatible material. The consumable container may also comprise at least one of: ethylene-vinyl acetate (EVA), polyvinyl chloride (PVC), or polyethylene (PE).

In some embodiments of the first aspect of the invention, the consumable container will comprise a laminate polymer construction. For example, one layer of the laminate construction might be safe for contact with the fluid, another might provide a gas boundary, and one might be suitable for heat sealing. This allows for combinations of different properties to be incorporated into the material of the consumable container.

The portions removed from the consumable container may be disposed within respective vials, and the one or more removable portions of the consumable container are preferably disposed within respective vials prior to said portions being removed. Said vials will preferably have respective lids. More preferably, the vials will be configured such that removal of the lid from a vial will unseal the removable portion disposed within. According to some embodiments said vials can be transported within a pneumatic tube system. However, the format of the sample must be suitable for the analysis system being used. Therefore, the one or more removable portions may only be disposed in respective vials if this is a format suitable for the analysis system being used.

Embodiments of the first aspect of the invention may also provide the one or more sealable, removable portions in the form of an array. However, the consumable container could also comprise a single sealable, removable portion.

Further embodiments of the first aspect of the invention provide for sampling vials, wherein the one or more sealable, removable portions are attached to respective vials prior to removal. Such embodiments avoid the need to dispose a sample within a vial.

According to a second aspect of the invention, a consumable container for filling with a fluid in a bioprocessing process is provided, which comprises one or more sealable portions, such that one or more samples of the fluid may be taken by sealing one or more of said portions, and wherein at least one of the sealable portions comprises an analytics region.

The analytics region may comprise reagents, such as lyophilised reagents, or other features to enable analysis of the bioprocess fluid to be conducted within the sealable portion. The additional features may, for example, be an optical detector, an electrochemical detector, a heating element, a cooling element, or a combination of these.

According to embodiments of the second aspect of the invention, the sealable portions may be removable.

Initially the bioprocess fluid is sealed from these reagents so that the reagents cannot come into contact with the bioprocess fluid. Such contact would risk contamination of the fluid, which is typically the product and may be infused into a patient later in the process. The fluid can be sampled into the analytical sealable portion when required, but still sealed from the reagents. The analytical sealable portion can then be sealed and removed from the system by any of the methods described in the previous invention. The sample is preferably brought into contact with the analytics region only once the sample region has been sealed from the bulk fluid. This ensures that reagents in the analytics region are kept separate from the bulk fluid, thereby preventing contamination of the bulk by the reagents.

In some embodiments this sampling will include a "loop" where the sample can both flow into and out of the analytical sealable portion. In other embodiments the sampling will be a "dead end" which contains a vacuum. In a further embodiment the sampling will be a "dead end" where the sampling region is compliant and initially collapsed. Filling will cause the sample region to inflate.

The analytical sealable portion can be made from rigid polymer in some embodiments. In other embodiments it may be made from thin flexible polymers heat sealed together. This has the advantage of eliminating dead volumes and reducing bubbles while also being low cost. This may be attached to a rigid chassis to simplify handling. Polymers could include ethylene-vinyl acetate (EVA), polyvinyl chloride (PVC), polypropylene (PP) or polyethylene (PE)

Following removal of such embodiments from the system, the bioprocess fluid can then pass through the steps required for analysis. These steps may be automated to avoid user variability. The first step may bring the fluid into the analytics region. This can be achieved by breaking a seal, for example a heat seal that is sufficient to avoid opening under normal processing pressures but when desired can be broken to allow fluid to flow past this seal. The heat seal could be broken by application of fluid pressure. In the "dead end" embodiment, this fluid pressure could be achieved by compressing the sample region, while in the "loop" embodiment this could be achieved by a drive fluid connected to the sample region. Alternatively, the separation of the fluid from the analytics region could be achieved by other methods, for example a valve such as a pinch valve. Another possibility is that it could be connected to a previously separate part of the system. In embodiments where the sealable portions are removable, the separation of the fluid from the analytics region may not be broken until after the sample region has been separated from the main portion of the consumable container.

In some embodiments of the second aspect of the invention, the one or more sealable portions may respectively comprise a sample region having an input end for receiving fluid and an output end, the sample region being connected to the analytics region. The input end of the sample region may be configured to receive fluid from a main portion of the consumable container and the output end to return fluid to said main portion. A valve may be disposed on the main portion between the input end of the sample region and the output end of the sample region, such that fluid is directed into the sample region when the valve is closed. The analytics region may be connected to the sample region via an inlet disposed between the input end of the sample region and the output end of the sample region. Alternatively, the input end of the sample region may be configured to receive fluid from a main portion of the consumable container and the analytics region may be connected to the sample region at the output end of the sample region. In embodiments where the sealable portions are also removable, the connection between the analytics region and the sample region may be sealed until the sample region has been separated from the main portion. The sealing of the analytics region from the sample region may achieved by a heat seal, and the heat seal may be opened by the application of fluid pressure created by compressing the sample region. The sealing of the analytics region from the sample region may be achieved by a pinch valve. The analytics region may include reagents. The analytics region may include lyophilised reagents. The analytics region may include an optical detector. The analytics region may include an electrochemical detector. The analytics region may include a thermal (calorimetric) detector. The analytics region may include a heating or cooling element.

In some embodiments the fluid may be brought into contact with liquid or dry reagents which may be dyes able to stain cells within the fluid. Possible dyes include DAPI, acridine orange, trypan blue, and calcein AM, or other dyes that may be useful for staining either live cells, dead cells, or both.

In other embodiments the reagents will allow for the detection of proteins for example through the use of an enzyme linked immunosorbent assay (ELISA).

In another embodiment the reagents will allow for a polymerase chain reaction so that the DNA can be amplified and later detected to determine the genetic identity of material in the fluid.

In some embodiments the fluid may then be moved to a separate interrogation region. This region may have a high optical quality to enable better detection using optical methods such as photodiodes, cameras or photo multiplier tubes. The region may be illuminated by a light source such as an LED, laser or incandescent bulb which may serve to enable the cells or other items to be observed or may cause them to fluoresce. Alternatively this detection may occur in the same location as the fluid is mixed with the reagents. Detection could alternatively be by electrochemical methods where electrodes functionalised with appropriate chemistry are embedded in the detection region to detect the desired analytes. In addition, detection could be by thermal (calorimetric) methods whereby heat emitted (exothermic) or absorbed (endothermic) by the fluid detects the desired analytes or the metabolic activity of cells.

According to a third aspect of the invention, a system is provided, the system including a reusable part, a bulk fluid container, and a consumable container according to the first aspect of the invention. The consumable container is arranged to be fluidly connected in use to the bulk fluid container such that the consumable container may be filled with a sample of the fluid from the bulk.

The system will preferably further comprise means for purging the consumable container and returning the fluid to the bulk container after the one or more removable portions have been removed.

Fluid may in some embodiments be transferred between the bulk container and the consumable container at least partially through the creation of a vacuum outside the disposable. Alternatively, where at least part of the disposable is rigid walled, fluid may be transferred between the bulk container and the consumable container by the creation of a vacuum within the disposable. Fluid may, in addition or alternatively, be transferred between the bulk container and the consumable container at least partially through the action of gravity by positioning the consumable container below the level of the fluid in the bulk container. Another possibility is for the fluid to be transferred between the bulk container and the consumable container at least partially through the use of a pump. The pump may be a peristaltic pump.

According to a fourth aspect of the invention, a system is provided for processing biological samples, the system comprising a first processing station having an outlet, a second processing station having an inlet, a pumped fluidic channel connecting said outlet to said inlet, wherein the second processing station comprises a consumable container, wherein the consumable container comprises one or more sealable, removable portions, such that one or more samples of the fluid may be taken by sealing and removing one or more of said portions.

BRIEF DESCRIPTION OF THE FIGURES

Some examples of consumable containers and systems for use in bioprocessing will now be described with reference to the accompanying drawings, in which:—

FIGS. 4a to 4d show the steps of a possible method for taking samples from a consumable container;

FIGS. 5a to 5d show the steps of another possible method for taking samples from a consumable container;

FIGS. 6a to 6d show the steps of a further possible method for taking samples from a consumable container;

FIGS. 7a to 7d show the steps of one method for disposing a sample in a vial, such that removing the lid from the vial allows access to the sample;

DETAILED DESCRIPTION

Figure 1:
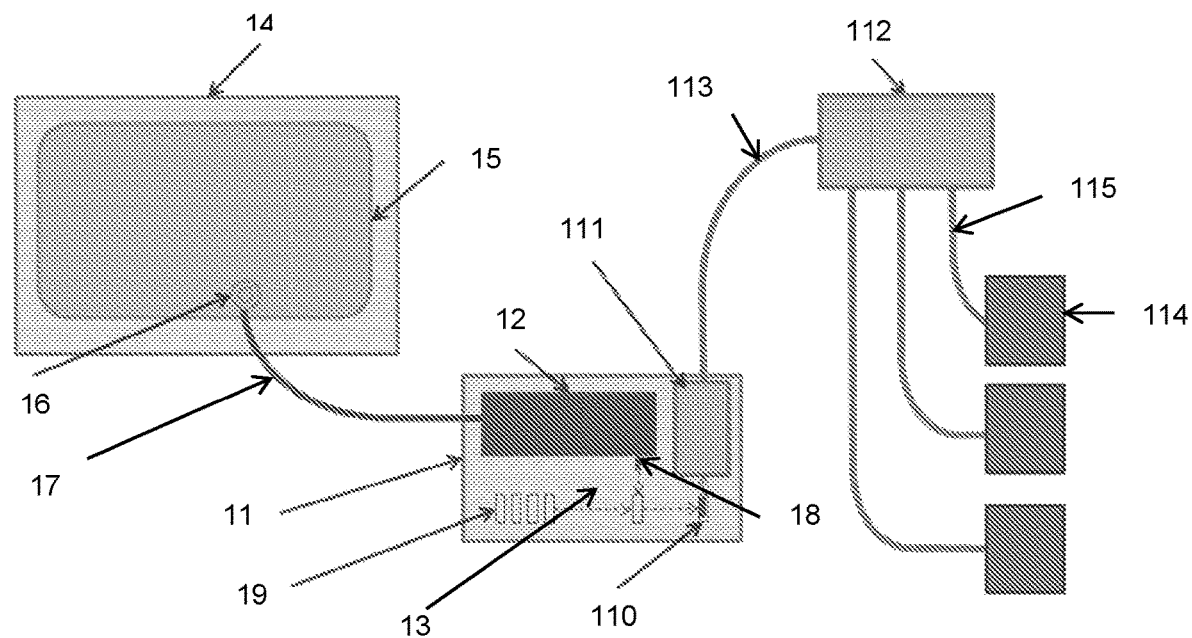
FIG. 1 shows an arrangement of components involved in taking samples in bioprocessing.

FIG. 1 shows an arrangement of components involved in taking samples in bioprocessing in which a sampling system 11 is connected to a bioprocessing system 14. System 11 is for isolating samples for analysis and includes a consumable container 12 and a reusable part 13. The consumable container 12 is consumed in the process of taking samples, said process being carried out by reusable part 13. The bioprocessing system 14 includes a bag 15 carrying the bulk product which is to be sampled, said bag having at least one sampling port 16. The bioprocessing system 14 provides a rocking motion to allow for mixing and gas transfer within bag 15 in order to promote cell growth.

The consumable part 12 of the system 11 is connected to sampling port 16 of bag 15 in the bioprocessing system 14 via a tube 17 during the initial setup of bioprocessing system 14 and remains connected for the duration of the bag's use.

The consumable part 12 of the system 11 can take different forms, but all generally include sealable, removable portions 18. This allows for samples of the fluid to be taken by sealing and removing one of the portions 18.

In the system depicted in FIG. 1, the consumable 12 is initially empty of any liquid or gas, and fluid is transferred from bag 15 to consumable 12 via tube 17. As a result of this fluid transfer, portions 18 also fill with fluid. When a sample is to be taken, one of these portions 18 is then sealed and separated from the main volume of consumable 12. The separated portion is then disposed within one of vials 19. Alternatively the removable portion 18 could be disposed within one of vials 19 before being sealed and removed.

Vial 110 carrying the sample is then moved to a transfer system sender module 111. Sender module 111 transfers vial 110 to transfer system router module 112 via intermediate tube 113. Router module 112 subsequently transfers vial 110 to one of a plurality of destinations 114 via respective tube 115. Destinations 114 may comprise one or more of: a lab, an automated analysis instrument, or a low temperature storage system. Alternatively vial 110 may be transported manually by a user.

Fluid transfer between the consumable container 12 and the bag 15 may occur as a result of any controllable fluid transfer method known in the art. One such method is the creation of an at least partial vacuum outside of the consumable container 12. The flexible nature of the walls of consumable container 12 will then cause the fluid to be drawn into consumable container 12. Control may be achieved by the action of a pinch valve acting on tube 17, or by controlling the strength of the vacuum. Another such method is to allow the fluid to flow under the action of gravity by putting consumable container 12 and bag 15 at different heights. Once again the fluid transfer may be controlled by a pinch valve acting on tube 17. Alternatively the fluid may be transferred using a non-contact pump, such as a peristaltic pump. Control of the fluid transfer is then provided by the pump itself acting on tube 17, although valves may also be used.

In the embodiment shown in FIG. 1, the fluid is purged from consumable container 12 after the sample has been taken and returned to bioprocessing system 14. This is to prevent the build-up of biological material in the consumable container 12 due to cell mortality. This purging of fluid from consumable container 12 may occur through any of the methods mentioned above. Following this it may be desirable to also purge tube 17 as cell mortality can lead to undesirable build-up of biological material in tube 17. This could be through a fluidic purge, introducing sterile fluid from an external source, or a gas purge, introducing a sterile gas from an external source. Alternatively, the periodic aspiration and evacuation of fluid from the tube 17 ensures that fluid in the tube is renewed, thereby preventing the negative effects of cell mortality. This should be conducted at least once every 4 hours. In order to achieve better washing this may be repeated more than once in short succession, and it may also be desirable to conduct this immediately prior to sampling to ensure that the fluid in the tube 17 is representative of the bulk product in bag 15.

Figure 2:
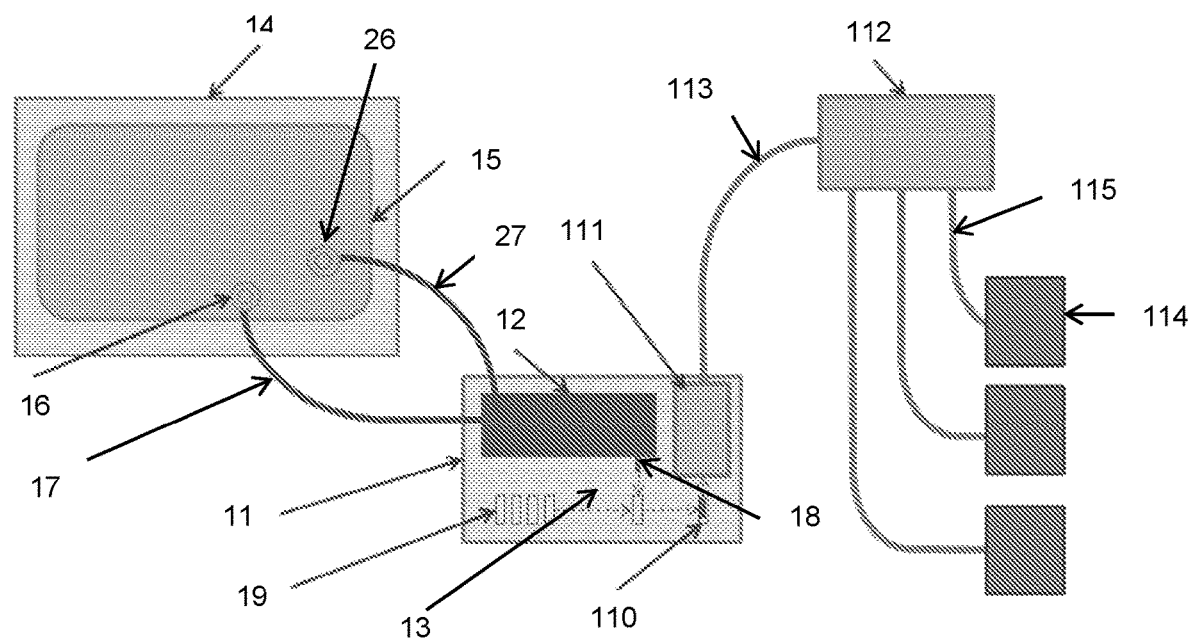
FIG. 2 shows another arrangement of components involved in taking samples in bioprocessing.

In other embodiments of the invention, the negative effects of cell mortality are avoided by recirculating the fluid, as is shown in FIG. 2. Instead of transferring the fluid between the bag 15 and the consumable container 12 via tube 17, the fluid enters the consumable container via tube 17 and returns to the bag 15 through port 26 via a different tube 27. This avoids the need to purge the tube 17 and the consumable container 12 and ensures that the fluid being sampled is always representative of the bulk product in bag 15.

Figure 3:
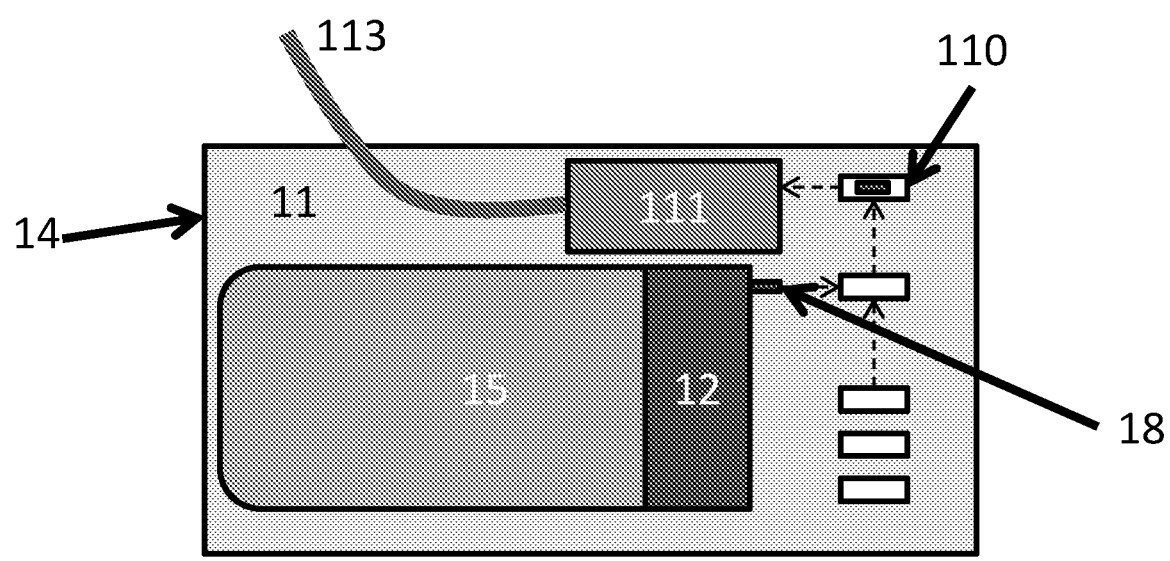
FIG. 3 shows still another arrangement of components involved in taking samples in bioprocessing.

Another alternative to the purging of consumable container 12 and tube 17 is for the sealable, removable portions 18 to be a part of bag 15 containing bulk product, the bag 15 being itself consumable. FIG. 3 shows an example of such an arrangement. Here the sampling system 11 is mounted onto the bioprocessing system 14, the bioprocessing system 14 applying a rocking motion to the product in bag 15. The bag 15 of FIG. 3 includes a consumable container portion 12, although in some embodiments the entire bag 15 is consumable. One of a plurality of sealable, removable portions 18 is removed when a sample is desired to be taken and is disposed within a vial 110 ready for transport. The vial is then moved to transfer sender module 111 which sends the vial 110 including sealable, removable portion 18 via tube 113. The benefit of this arrangement is that there is no need for tubes 17 and 27, and because the bag 15 itself includes the consumable container portion 12 the product in consumable container 12 is kept moving, avoiding the negative effects of cell mortality.

In all embodiments of the invention the consumable container 12 will usually comprise a material suitable for biocompatibility and, as will be seen below, in certain embodiments the consumable container 12 will comprise a material suitable for heat sealing. Examples of possible materials include: ethylene-vinyl acetate (EVA), polyvinyl chloride (PVC), or polyethylene (PE). The consumable container could also comprise a laminate polymer construction, wherein one layer of the laminate construction might be safe for contact with the fluid, another might provide a gas boundary, and one might be suitable for heat sealing. This allows for combinations of different properties to be incorporated into the material of the consumable container.

FIGS. 4a to 6d show different possible arrangements of the sealable, removable portions 18.

FIGS. 4a to 4d show an arrangement in which the removable portions 18 are connected in parallel to a common transverse part 31. This transverse part 31 may be the consumable container 12 (or the bag 15 in embodiments where this is the consumable container) itself, with the removable portions 18 extending outwards from the consumable container 12, or the transverse part 31 may be separate from the consumable container.

In FIG. 4a three of the portions 18 have been reversibly sealed, for example by pinching, as shown by arrows 32. The arrow indicates the influx of fluid, which then fills the open portion 33. In FIG. 4b the previously open portion 33 has been sealed. The sealing may occur through application of heat. In such embodiments, an automatic heat sealer using two heated metal plates, for example controlled by a microprocessor, adheres opposing layers of the portions 33 together, as shown by region 34. Alternatively, a physical aseptic connector can be used to connect portions 18 to transverse part 31. In such embodiments, the connectors may be closed to seal of portions 18 which are not being removed, and left open to allow the portion 33 being removed to be filled with fluid. The connector would then be closed after filling.

FIG. 4c shows the portion 33 being removed. In embodiments where the portion 33 has been heat sealed this achieved by physically cutting along the sealed region 34, while in embodiments using a physical connector the portion 33 can be easily disconnected. The result of removing portion 33 is shown in FIG. 4d. After this step the other portions 18 can be reopened so that the process may be repeated.

FIGS. 5a to 5d and 6a to 6d show two different arrangements of sealable, removable portions 18 connected in series, FIGS. 5a to 5d showing the arrangement when portions 18 are sealed using heat and then separated from the consumable container 18, whilst FIGS. 6a to 6d show the arrangement when portions 18 are connected to the consumable container 18 using physical aseptic connectors.

The first step of taking a sample when the portions 18 are sealed using heat is shown in FIG. 5a. A region 41 of consumable container 12 is filled with fluid, as shown by the arrow in the figure. Region 41 could extend from the consumable container 12, or it could be the consumable container 12 itself.

FIG. 5b shows the step of sealing off a sampling portion 42 from the region 41. The sampling portion shown is illustrative, and need not be an end of the region 41. It could instead be, for example, a corner of the region 41. As shown in FIG. 5c the sampling portion 42 is then separated from the region 41, for example by cutting.

After the sampling portion 42 has been separated from the region 41, the region 41 is purged, as shown by the arrow in FIG. 5d. The process may then be repeated.

The first step of taking a sample when the portions 18 are connected using physical connectors is shown in FIG. 6a. A region 51 of consumable container 12 is filled with fluid, as shown by the arrow in the figure. Region 51 could be the consumable container 12 itself, but typically takes the form of a string of sampling portions linked together by physical connectors connected to the consumable container 12 at one end.

In FIG. 6b a sampling portion 52 is sealed off from region 51 by closing a physical connector, and the sampling portion 52 is then separated from region 51 in FIG. 6c. Finally, in FIG. 6d the region 51 is purged in order that the process might be repeated, as shown by the arrow in FIG. 6d.

As mentioned earlier the samples taken from the consumable container 12 are disposed within vials, and an example of this is shown in FIGS. 7a to 7d. In FIG. 7a the sampling portion 61 is disposed in the vial 62 before the sample is taken. The sampling portion 61 is disposed in the vial 62 through a region 63 of the lid 64 of the vial, leaving a region 65 of the consumable container outside of the vial. The sampling portion is then aspirated as shown by the arrow in FIG. 7a.

In the step shown in FIG. 7b heat is applied to the region 63. This seals the sampling portion 61 off from the region 65 of the consumable container, and also acts to integrate the sampling portion 61 with the vial 62 via lid 64. The composite 66 of the vial and the sampling portion is then separated from the region 65 in the step shown in FIG. 7c.

Removing the lid 64 from a composite vial 66 will serve to allow access to the sample, and this is illustrated in FIG. 7d. The region 63 is sealed to the portion 61 when heat is applied. Therefore, when the lid 64 is removed from the composite vial 66 the seal is broken, allowing access to the sample.

Figure 8A:
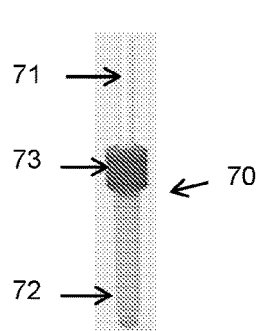
FIGS. 8a to 8e show the steps of an alternative method for disposing a sample in a vial, wherein the vials are supplied attached to the consumable container.
Figure 8B:
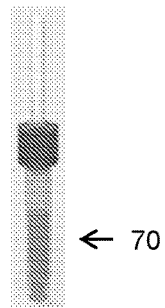

An alternative means of disposing the samples in vials is shown in FIGS. 8a-8e. The sampling vial 70 shown in FIG. 8a comprises an extended part 71 of the consumable container, a vial body 72, and a lid 73. The extended part 71 is attached to the lid 73, and the sampling vial 70 is therefore supplied attached to the consumable container. FIG. 8b shows the sampling vial 70 after it has been aspirated with a sample.

Figure 8C:
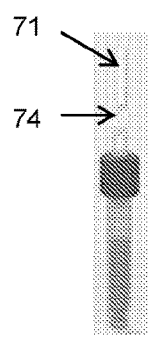
Figure 8D:
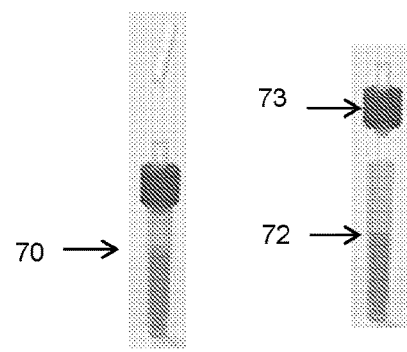
Figure 8E:
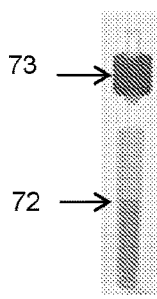

In the step shown in FIG. 8c heat has been applied to region 74 of the extend part 71, thereby sealing off the sampling vial from the bulk product in the consumable container. In FIG. 8d the sampling vial 70 has been separated from the consumable container, which is typically achieved by cutting. The sampling vial 70 may now be transported, and the sample accessed by removing the lid 73 from the vial body 72, as shown in FIG. 8e.

Figure 9:
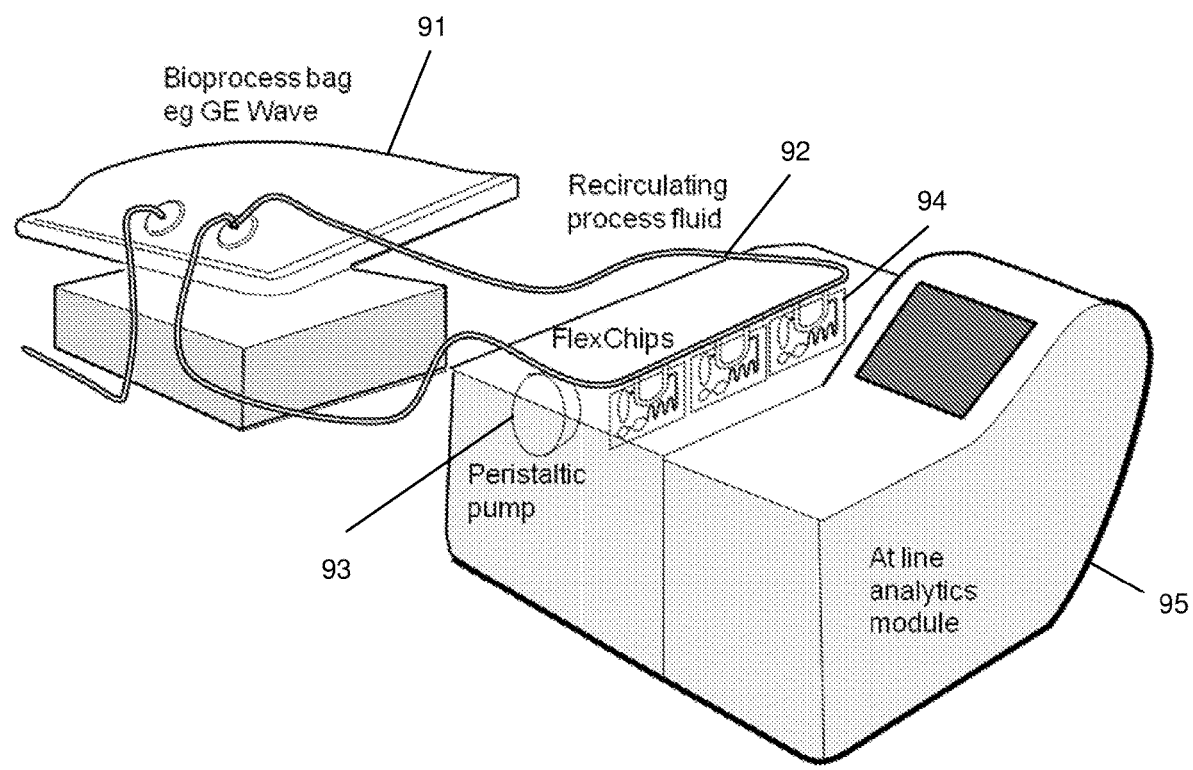
FIG. 9 shows the separable portions as part of a bioprocessing system.

FIG. 9 shows separable portions 94 as part of a bioprocessing system. The system includes a bulk fluid container 91, which may be a bioprocessing bag such as a GE Wave bag. A tube 92 circulates fluid received from the bulk fluid container 91 by means of a peristaltic pump 93. The separable portions 94 then collect the fluid from the tube 92. The separable portions 94 comprise an analytics region to enable automated analysis in situ by the analytics module 95.

Figure 10:
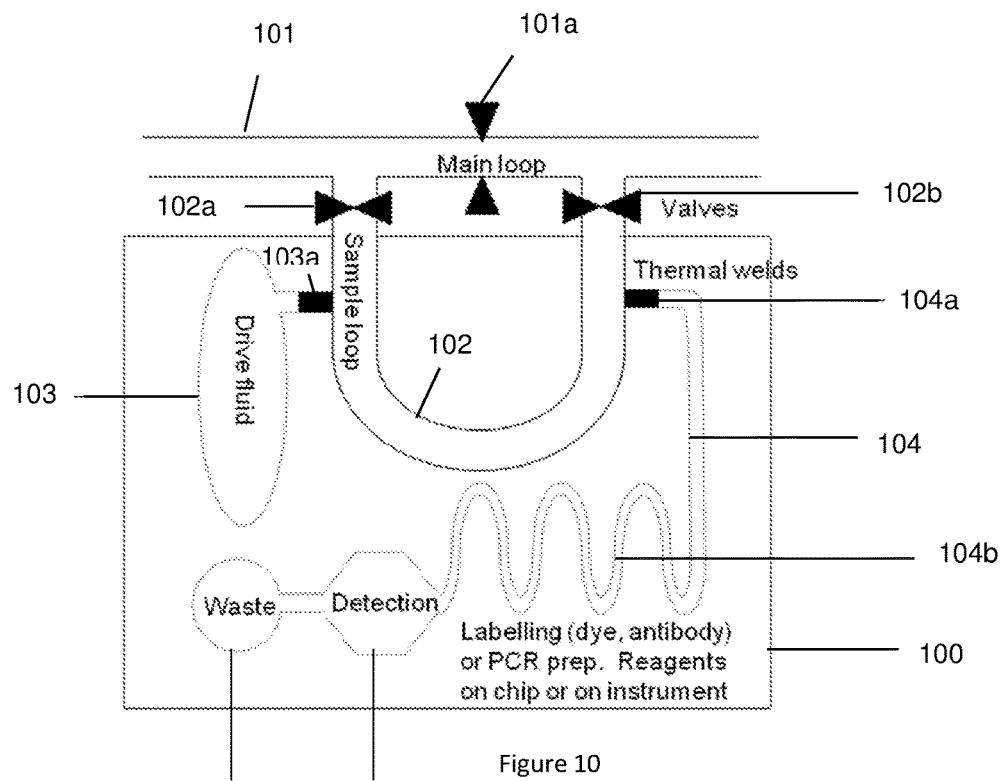
FIG. 10 shows an example of a separable portion which includes an analytics region.

FIG. 10 shows an embodiment of a separable portion 100 connected to a main loop 101. The main loop receives and circulates fluid from a bulk fluid container, and this fluid is then collected by one or more separable portions 100. A sample loop 102 is connected to the main loop 101 via an inlet valve 102a and an outlet valve 102b. Disposed on the main loop 101 between the valves 102a and 102b is a valve 101a. Adjacent to the input end of the sample loop is a thermal weld 103a separating the sample loop from drive fluid 103.

An analytics region is separated from the sample loop by a thermal weld 104a disposed adjacent to the output end of the sample loop. The analytics region comprises a labelling region 104b, a detection region 104c, and a waste region 104d. The labelling may be done by dyes, antibodies, or PCR prep, and these reagents may be included on the chip, or the reagents could be provided by a separate instrument.

The valves 101a, 102a and 102b and the drive fluid 103 are typically coupled to actuators in a separate analytics module. These actuators may be pneumatic or electromechanical. The analytics module also includes a detection system coupled to the detection region 104c, for example an optical detector and emitter.

Figure 11:
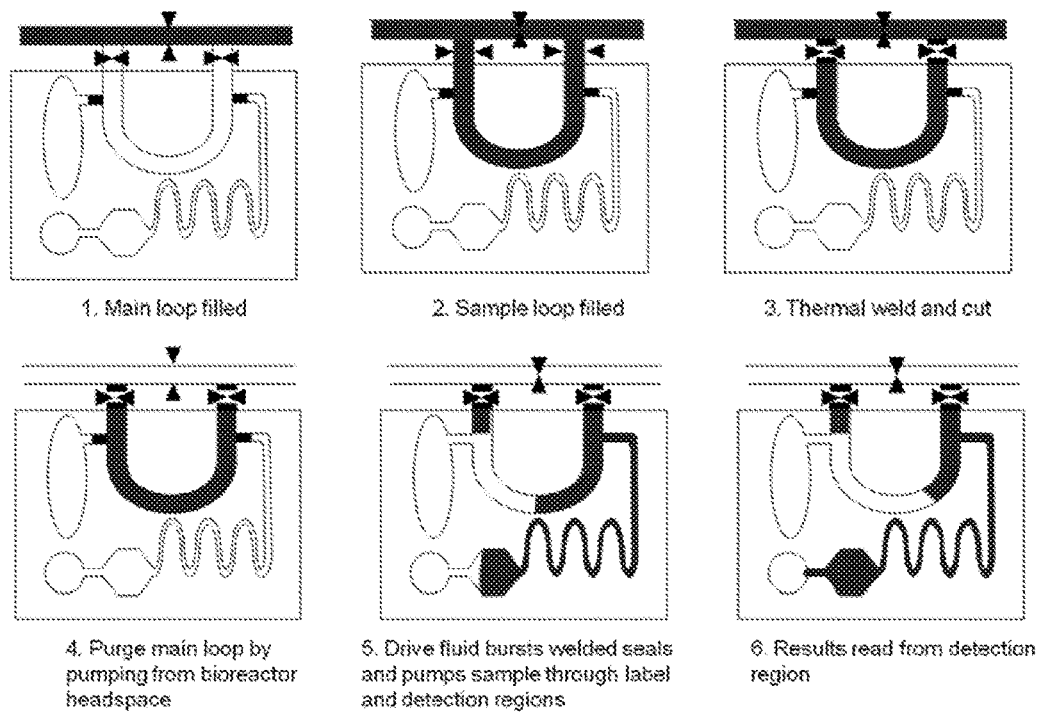
FIG. 11 shows the operation of a separable portion which includes an analytics region.

FIG. 11 shows the separable portion 100 in operation. In the first step, bioprocess fluid fills the main loop 101, but cannot enter the separable portion because the valves 102a and 102b are closed. In step 2, the main loop valve 101a is closed and the valves 102a and 102b are opened, allowing fluid to enter the sample region 102. The valves 102a and 102b or other actuators in a similar location then heat seal and cut the separable portion 100 in step 3, disconnecting it from the main loop. In step 4, the main loop 101 can then be purged, for example by pumping through gas from the headspace. However, step 4 may, in some embodiments, be skipped. In step 5, the drive fluid 103 is compressed with an actuator, breaking the heat seal 103a and causing the fluid in the sample region to break heat seal 104a and flow into the analytics region 104. The fluid flows via labelling region 104b, where it collects reagents such as dyes, into detection region 104c. In step 6, the fluid in the detection region is analysed.

Figure 12:
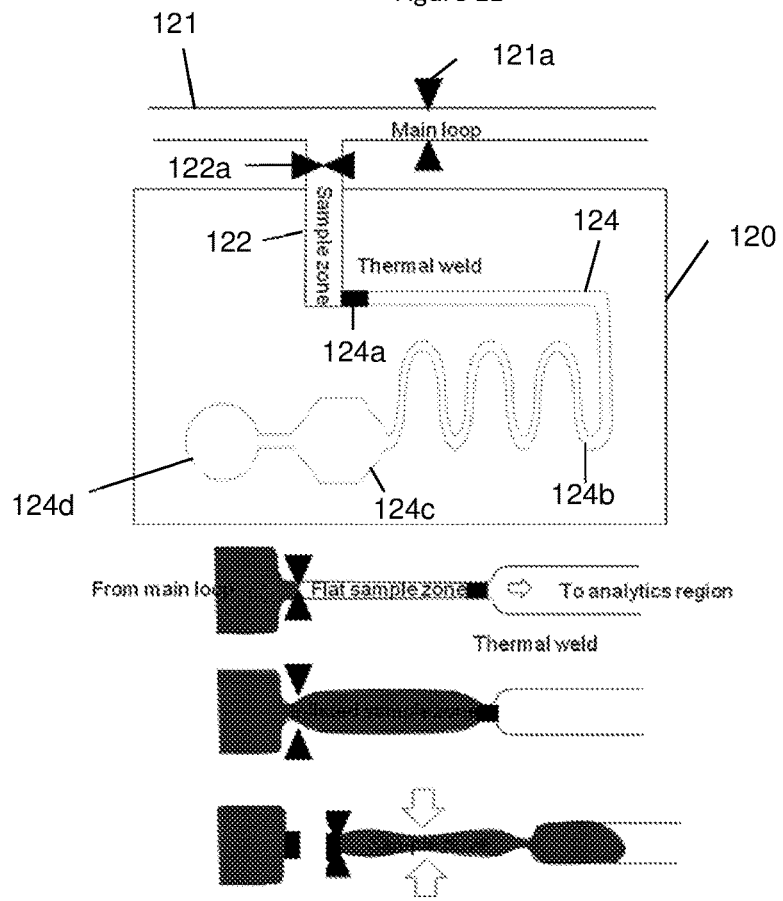
FIG. 12 shows another example of a separable portion which includes an analytics region, and the operation of that separable portion.

FIG. 12 shows an alternative embodiment of a separable portion 120 where the sample fluid fills a flexible dead end sample region 122. This is achieved by closing a valve 121a, provided on the main loop 121 downstream of the input end of the sample region 122, and opening a valve 122a in the separable portion to allow the sample region 122 to inflate. The valve 122a in the separable portion can then be closed, heat sealed, and cut. The sample can then be compressed with an actuator breaking a heat seal 124a and causing the fluid to flow into the labelling region 124b as before.

The invention claimed is:

1. A consumable container for filling with a fluid in a bioprocessing process, comprising:
at least one sealable, removable portion, such that one or more samples of the fluid may be taken by sealing and removing said at least one sealable, removable portion;
wherein each of the at least one sealable, removable portion removed from the consumable container is disposed within a respective vial;
wherein said respective vial has a respective lid;
wherein said respective vial is configured such that removal of the respective lid from the respective vial unseals the at least one sealable, removable portion disposed within.

2. The consumable container of claim 1, wherein the at least one sealable, removable portion is sealed by application of heat to an area between the at least one sealable, removable portion and a remainder of the consumable container.

3. The consumable container of claim 1, wherein the at least one sealable, removable portion is separated from a remainder of the consumable container by at least one respective physical, aseptic connector, said at least one connector allowing sealing and removal of the at least one sealable, removable portion.

4. The consumable container of claim 2, wherein the consumable container comprises a heat sealable material.

5. The consumable container of claim 1, wherein the at least one sealable, removable portion comprises a plurality of sealable, removable portions connected to a common transverse part in parallel.

6. The consumable container of claim 1, wherein the at least one sealable, removable portion comprises a plurality of sealable, removable portions connected in series.

7. The consumable container of claim 1, wherein the consumable container comprises a biocompatible material.

8. The consumable container of claim 1, wherein the consumable container comprises at least one of: ethylene-vinyl acetate (EVA), polyvinyl chloride (PVC), or polyethylene (PE).

9. The consumable container of claim 1, wherein the consumable container comprises a laminated polymer construction.

10. The consumable container of claim 1, wherein the at least one sealable, removable portion is attached to the respective vial prior to removal.

11. The consumable container of claim 1, wherein each of the at least one sealable, removable portion of the consumable container is disposed within the respective vial prior to removal.

12. The consumable container of claim 1, wherein said vial can be transported within a pneumatic tube system.

13. The consumable container of claim 1, wherein the at least one sealable, removable portion comprises a plurality of sealable, removable portions that form an array.

14. The consumable container of claim 1, wherein the at least one sealable, removable portion comprises an analytics region.

15. The consumable container of claim 14, wherein the analytics region contains reagents.

16. The consumable container of claim 14, wherein the at least one sealable, removable portion comprises a sample region having an input end for receiving fluid and an output end, the sample region being connected to the analytics region.

17. The consumable container of claim 16, wherein the input end of the sample region is configured to receive fluid from a main portion of the consumable container and the output end is configured to return fluid to said main portion.

18. The consumable container of claim 17, wherein a valve is disposed on the main portion between the input end of the sample region and the output end of the sample region, such that fluid is directed into the sample region when the valve is closed.

19. The consumable container of claim 18, wherein the analytics region is connected to the sample region via an inlet disposed between the input end of the sample region and the output end of the sample region.

20. The consumable container of claim 16, wherein the input end of the sample region is configured to receive fluid from a main portion of the consumable container and the analytics region is connected to the sample region at the output end of the sample region.

21. A system including a reusable part, a bulk fluid container, and a consumable container according to claim 1, wherein the consumable container is arranged to be fluidly connected in use to the bulk fluid container such that the consumable container may be filled with a sample of the fluid from the bulk fluid container.

22. The system of claim 21, further comprising means for purging the consumable container and returning the fluid to the bulk fluid container after the at least one sealable, removable portion has been removed.

23. The system of claim 21, wherein fluid can be transferred between the bulk fluid container and the consumable container at least partially through the creation of a vacuum.

24. The system of claim 21, wherein fluid can be transferred between the bulk fluid container and the consumable container at least partially through the action of gravity by positioning the consumable container below the level of the fluid in the bulk fluid container.

25. The system of claim 21, wherein fluid can be transferred between the bulk fluid container and the consumable container at least partially through the use of a pump.

26. The system of claim 25, wherein the pump is a peristaltic pump.

* * * * *